(12) United States Patent
Phan et al.

(10) Patent No.: US 12,102,424 B2
(45) Date of Patent: Oct. 1, 2024

(54) REAL-TIME MONITORING OF COVID-19 PROGRESS USING MAGNETIC SENSING AND MACHINE LEARNING

(71) Applicant: University of South Florida, Tampa, FL (US)

(72) Inventors: Manh-Huong Phan, Tampa, FL (US); Kee Young Hwang, Wesley Chapel, FL (US); Valery Ortiz Jimenez, Tampa, FL (US); Baleeswaraiah Muchharla, Tampa, FL (US)

(73) Assignee: University of South Florida, Tampa, FL (US)

( * ) Notice: Subject to any disclaimer, the term of this patent is extended or adjusted under 35 U.S.C. 154(b) by 498 days.

(21) Appl. No.: 17/331,761

(22) Filed: May 27, 2021

(65) Prior Publication Data

US 2021/0369137 A1  Dec. 2, 2021

Related U.S. Application Data (60) Provisional application No. 62/704,779, filed on May 28, 2020.

(51) Int. Cl.
*A61B 5/08* (2006.01)
*A61B 5/00* (2006.01)
(Continued)

(52) U.S. Cl.
CPC .............. *A61B 5/0809* (2013.01); *A61B 5/05* (2013.01); *A61B 5/4842* (2013.01);
(Continued)

(58) Field of Classification Search
CPC ....... A61B 5/0809; A61B 5/05; A61B 5/4842; A61B 5/7267; A61B 5/7282;
(Continued)

(56) References Cited

U.S. PATENT DOCUMENTS 5,825,293 A * 10/1998 Ahmed ................... A61B 5/113
600/534
7,835,785 B2  11/2010 Scully et al.
(Continued)

OTHER PUBLICATIONS

Wang [Abnormal respiratory patterns classifier may contribute to large-scale screening of people infected with COVID-19 in an accurate and unobtrusive manner, Researchgate, Feb. 2020] (Year: 2020).*

(Continued)

*Primary Examiner* — Oommen Jacob
(74) *Attorney, Agent, or Firm* — Meunier Carlin & Curfman LLC (57) ABSTRACT

A breathing monitor that includes a contactless sensor that uses magneto-LC resonance technology is provided. The breathing monitor collects breathing data from a patient that indicates a breathing pattern of the patient. A model trained using machine learning using breathing patterns collected from patients known to have different stages of COVID-19 is used to process the collected breathing data and to determine whether the patient has COVID-19. The model further determines the stage of COVID-19. The breathing monitor can identify likely COVID-19 infections faster than existing tests and requires no contact between the patient and a medical professional, which is an improvement over existing COVID-19 detection technologies.

10 Claims, 7 Drawing Sheets

(51) Int. Cl.
*A61B 5/05* (2021.01)
*G01N 27/74* (2006.01)
*G01N 33/497* (2006.01)
*G06N 20/00* (2019.01)
*G16H 10/60* (2018.01)
*G16H 40/67* (2018.01)
*G16H 50/20* (2018.01)
*G16H 50/50* (2018.01)
*G16H 50/70* (2018.01)
*G16H 70/60* (2018.01)

(52) U.S. Cl.
CPC .......... *A61B 5/7267* (2013.01); *A61B 5/7282* (2013.01); *G01N 27/74* (2013.01); *G01N 33/497* (2013.01); *G06N 20/00* (2019.01); *G16H 10/60* (2018.01); *G16H 40/67* (2018.01); *G16H 50/20* (2018.01); *G16H 50/50* (2018.01); *G16H 50/70* (2018.01); *G16H 70/60* (2018.01); *G01N 33/4975* (2024.05)

(58) Field of Classification Search
CPC .. G01N 33/497; G01N 33/4975; G06N 20/00; G16H 10/60; G16H 40/67; G16H 50/20; G16H 50/50; G16H 70/60
See application file for complete search history.

(56) References Cited

U.S. PATENT DOCUMENTS

| | | | | |
|---|---|---|---|---|
| 8,732,096 | B1* | 5/2014 | Glukhov | G16H 50/20 706/12 |
| 11,103,151 | B2* | 8/2021 | Rappaport | A61B 5/0044 |
| 2002/0107452 | A1* | 8/2002 | Kwong | G16H 40/67 600/509 |
| 2005/0107681 | A1 | 5/2005 | Griffiths | |
| 2012/0197539 | A1 | 8/2012 | Slupsky | |
| 2012/0310053 | A1* | 12/2012 | Henning | A61B 6/527 600/407 |
| 2014/0153795 | A1* | 6/2014 | Lenox | G06T 7/0012 382/128 |
| 2015/0335268 | A1* | 11/2015 | Biber | A61B 5/6892 600/411 |
| 2015/0369795 | A1* | 12/2015 | Tsow | G01N 33/497 73/23.3 |
| 2016/0147974 | A1* | 5/2016 | Sha | G16H 10/20 705/2 |
| 2019/0223782 | A1* | 7/2019 | Wen | A61B 5/0816 |
| 2019/0353639 | A1* | 11/2019 | Bazemore | A61B 5/082 |
| 2020/0029862 | A1 | 1/2020 | Phan et al. | |
| 2021/0369137 | A1* | 12/2021 | Phan | G16H 40/67 |
| 2022/0262514 | A1* | 8/2022 | Lure | G16H 50/70 |
| 2022/0280028 | A1* | 9/2022 | Moretti | A61B 1/00105 |

OTHER PUBLICATIONS

Thiabgoh [A new contactless magneto-LC resonance technology for real-time respiratory motion monitoring, Sensors and Actuators A 265 (2017) 120-126]. (Year: 2017).*

Wynants [Prediction models for diagnosis and prognosis of covid-19 infection: systematic review and critical appraisal, BMJ 2020; 369:m1328, Apr. 2020]. (Year: 2020).*

A. Olivares, G. Olivares, F. Mula, J.M. Górriz, J. Ramírez, Wagyromag: Wireless sensor network for monitoring and processing human body movement in healthcare applications, Journal of Systems Architecture, vol. 57, Issue 10, 2011, pp. 905-915, ISSN 1383-7621, https://doi.org/10.1016/j.sysarc.2011.04.001.

Latif, Siddique; Usman, Muhammad; Manzoor, Sanaullah; Iqbal, Waleed; Qadir, Junaid; Tyson, Gareth; et al. (2020): Leveraging Data Science To Combat COVID- 19: A Comprehensiveview. TechRxiv. Preprint. https://doi.org/10.36227/techrxiv.12212516.v1.

* cited by examiner

REAL-TIME MONITORING OF COVID-19 PROGRESS USING MAGNETIC SENSING AND MACHINE LEARNING

CROSS-REFERENCE TO RELATED APPLICATIONS

This application claims the benefit of priority to U.S. Provisional Patent Application No. 62/704,779, filed on May 28, 2020, entitled "REAL-TIME MONITORING OF COVID-19 PROGRESS USING MAGNETIC SENSING AND MACHINE LEARNING," the contents of which are hereby incorporated by reference in its entirety.

FIELD

The disclosure generally relates to methods and systems for monitoring breathing symptoms of a virus at various stages of disease progress.

BACKGROUND

Corona virus 2019 (COVID-19) has already killed more than 3 million people around the world a number which continues to increase exponentially daily. This outbreak represents an unprecedented global public health challenge. To limit the spread of COVID-19 and help doctors in clinical decision-making, the detection and real-time monitoring of their symptoms and growth at all (early, intermediate, and severe) states is critical. Common symptoms of COVID-19 include: (i) shortness of breath or difficulty breathing, (ii) cough, and (iii) fever. Numerous medical devices have been developed to diagnose COVID-19, but these devices provide inaccurate or limited information and usually possess lengthy processing time (30 minutes or longer) or are physically connected to patients. Therefore, there is an urgent need for developing contactless devices that enable early and fast detection of COVID-19 and track their growth rates in real time.

SUMMARY

A breathing monitor that includes a contactless sensor that uses magneto-LC resonance technology is provided. The breathing monitor collects breathing data from a patient that indicates a breathing pattern of the patient. A model trained using machine learning using breathing patterns collected from patients known to have different stages of COVID-19 is used to process the collected breathing data and to determine whether the patient has COVID-19. The model further determines the stage of COVID-19. The breathing monitor can identify likely COVID-19 infections faster than existing tests and requires no contact between the patient and a medical professional, which is an improvement over existing COVID-19 detection technologies.

In an embodiment, a system is provided. The system includes a breathing monitor and a diagnosis engine. The breathing monitor includes a magnet affixed to a patient and a non-contact sensor that measures impedance caused by a magnet field associated with the magnet. The breathing monitor outputs breathing data indicative of a breathing pattern of the patient based on impedance measurements from the non-contact sensor. The diagnosis engine receives the breathing data; retrieves a model associated with a disease; and diagnoses the patient with the disease using the model and the breathing data.

Embodiments may include some or all of the following features. The disease may be COVID-19. The sensor may include a Hall effect sensor or a magneto-LC resonance sensor.

In an embodiment, a method for remote disease diagnosis based on breathing data is provided. The method includes: receiving breathing data at a computing device through a network, wherein the breathing data comprises data indicative of a breathing pattern of a patient; retrieving a model associated with a disease by the computing device; and diagnosing the patient with the disease using the model and the breathing data.

Embodiments may include some or all of the following features. The disease may be COVID-19. Diagnosing the disease may include diagnosing a stage associated with the disease. The method may further include: receiving medical data associated with the patient; and diagnosing the patient with the disease using the model, the breathing data, and the medical data. The medical data may further include one or more of age and weight. The breathing data may be received from a breathing monitor. The breathing monitor may include: a magnet affixed to the patient; and a non-contact sensor. The sensor may include a Hall effect sensor or a magneto-LC resonance sensor. The method may further include: receiving first data indicative of breathing patterns of a plurality of patients known to have the disease; receiving second data indicative of breathing patterns of a plurality of patients known not to have the disease; and training the model using the first and second data.

In an embodiment, a method for diagnosing a disease based on breathing patterns is provided. The method includes: attaching breathing monitor to a patient; collecting breathing data from the breathing monitor by a computing device, wherein the breathing data comprises data indicative of a breathing pattern of the patient; retrieving a model associated with a disease by the computing device; and diagnosing the patient with the disease using the model and the breathing data by the computing device.

Embodiments may include some or all of the following features. The disease may be COVID-19. Diagnosing the disease may include diagnosing a stage associated with the disease. The method may further include: receiving medical data associated with the patient; and diagnosing the patient with the disease using the model, the breathing data, and the medical data. The medical data may include one or more of age and weight. The breathing monitor may include: a magnet affixed to the patient; and a non-contact sensor. The sensor may include a Hall effect sensor or a magneto-LC resonance sensor. The method may further include: receiving first data indicative of breathing patterns of a plurality of patients known to have the disease; receiving second data indicative of breathing patterns of a plurality of patients known not to have the disease; and training the model using the first and second data.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The accompanying drawings, which are in and constitute a part of this specification, illustrate certain examples of the present disclosure and together with the description, serve to explain, without limitation, the principles of the disclosure. Like numbers represent the same element(s) throughout the figures.

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Unless defined otherwise, all technical and scientific terms used herein have the same meaning as commonly understood to one of ordinary skill in the art to which this invention belongs. As used in the specification and claims, the singular form "a," "an," and "the" include plural references unless the context clearly dictates otherwise. As used herein, the terms "can," "may," "optionally," "can optionally," and "may optionally" are used interchangeably and are meant to include cases in which the condition occurs as well as cases in which the condition does not occur. Publications cited herein are hereby specifically incorporated by reference in their entireties and at least for the material for which they are cited.

Figure 1:
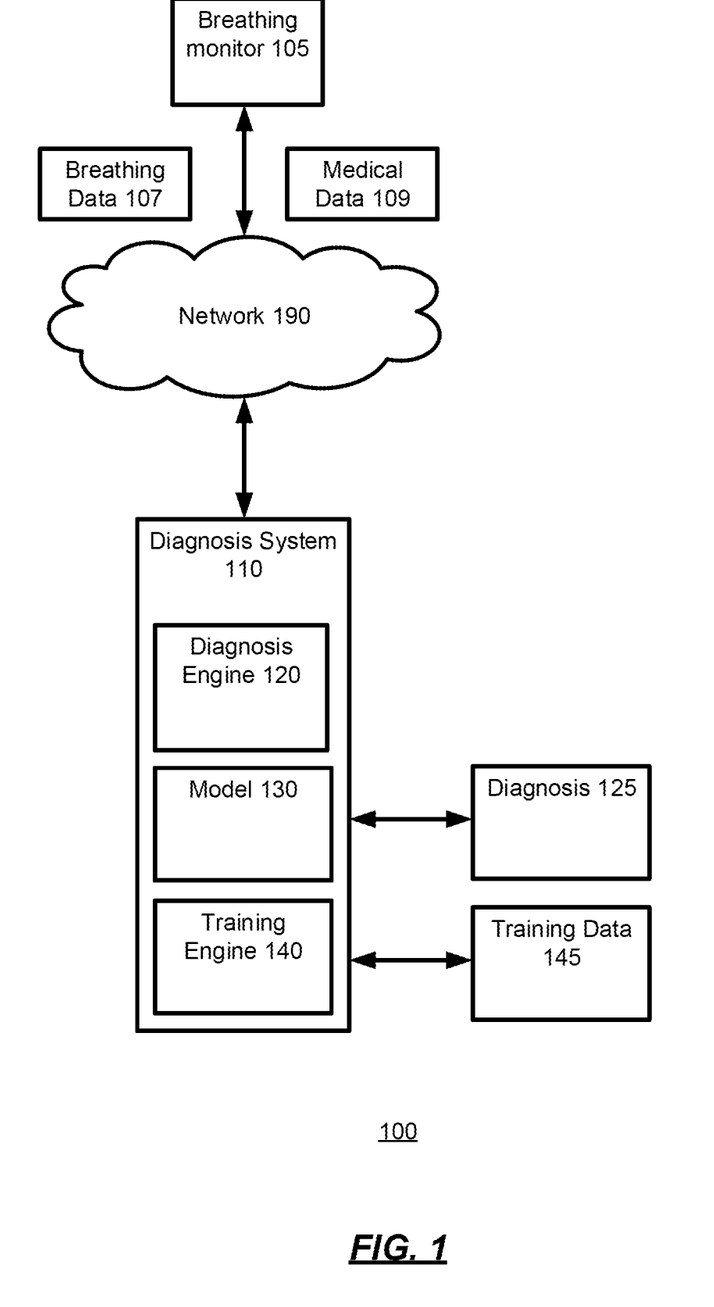
FIG. 1 is an illustration of an example environment for diagnosing a disease using a contactless sensor.

FIG. 1 is an illustration of environment 100 for diagnosing a disease using a contactless sensor. As shown, the environment 100 includes a breathing monitor 105 in communication with a diagnosis system 110 through a network 190. The network 190 may include a variety of public and private networks such as the internet, for example.

The breathing monitor 105 may collect breathing data 107 from a patient. In some embodiments, the collected breathing data may be a waveform whose frequency and amplitude represents a breathing pattern associated with the patient. The breathing monitor 105 may collect approximately 60 seconds of breathing data 107 from the patient at a time, and may transmit the collected breathing data 107 to the diagnosis system 110 through the network 190. Other time durations may be used.

Figure 2:
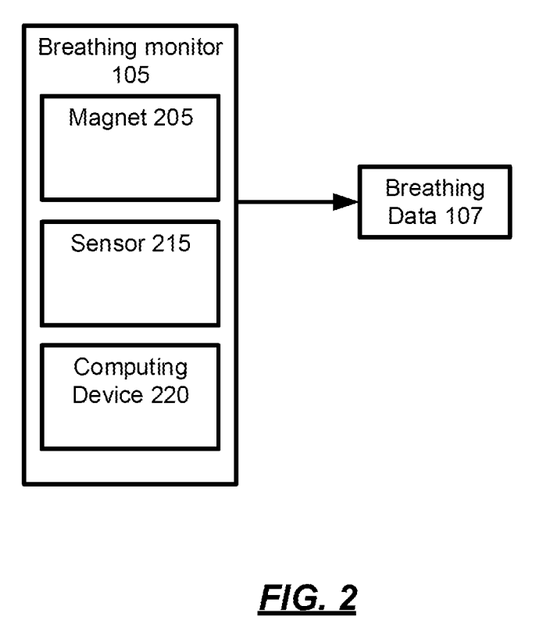
FIG. 2 is an illustration of an example breathing monitor.

Continuing to FIG. 2 is an example breathing monitor 105 that may be used. As shown, the breathing monitor 105 includes a magnet 205, a magnetic sensor 215, and a computing device 220. The magnet 205 may be a NdFeB magnet that is affixed to the skin of the patient. Other types of magnets may be used. The magnet 205 may be placed on the skin of the patient at a location such that the magnet will rise and fall as the patient breathes. The magnet 205 may be affixed to the patient using an adhesive, for example.

The sensor 215 may be placed near the magnet 205 and may detect a change in the position of the magnet 205 due to the breathing of the patient. In one embodiment, the sensor 215 may be a Hall effect sensor that measures a magnetic flux change due to the movement of the magnet 205 on the patient. In another embodiment, the sensor 215 may be a magneto-LC resonance ("MLCR") sensor that measures a change in impedance caused by the changing magnetic field due to the movement of the magnet 205 on the patient. Other types of sensors may be used.

The sensor 215 may be placed above the magnet 205. The sensor 215 may be a non-contact sensor 215 that does touch the skin or any other part of the patient. In some embodiments, the sensor 215 may be placed at approximately 5 cm from the magnet 205. Other distances may be used. The sensor 215 may measure the change in impedance due to movement of the magnet 205 with a frequency of approximately 80 Hz. Other frequencies may be used.

The computing device 220 may receive the output of the sensor 215 and may generate the breathing data 107 based on the output of the sensor 215. The computing device 220 may store the breathing data 107 for the patient, and/or may transmit the generated breathing data to the diagnostic system 110. An example computing device 220 is the computing device 700 illustrated with respect to FIG. 7.

Figure 3:
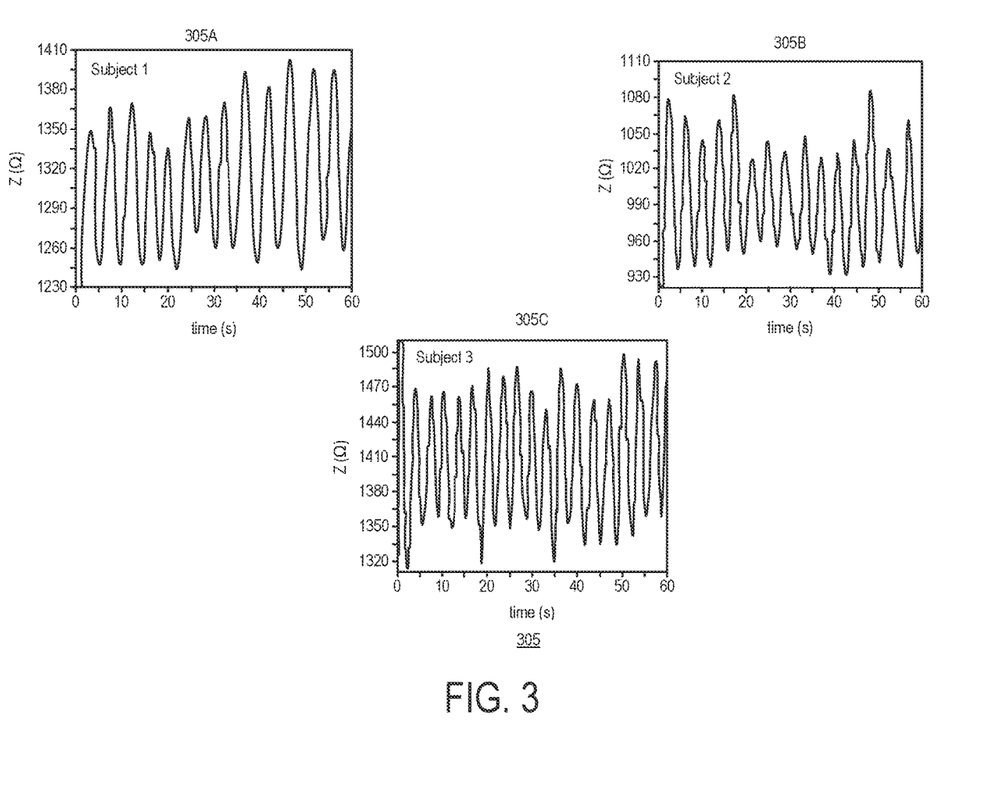
FIG. 3 is an illustration of example graphs of breathing data.

For example, with reference to FIG. 3 are three graphs 305 (e.g., the graphs 305A, 305B, and 305C) that each represent breathing data 107 collected from a patient or subject. Each graph of the graphs 305 shows the impedance measured by the sensor 215 over a one minute interval. As can be seen the peaks and troughs of each graph represent the depth of each breath, while the wavelengths represent the length of each breath.

With respect to the MLCR sensor 215, a conventional magneto-inductive coil induces a voltage between the ends of a non-magnetic conductor when a DC current is flowing through it. This phenomenon may be used to sense external magnetic fields. However, instead of using a non-magnetic wire (e.g., Cu) to make the inductive coil, in some embodiments, to enhance efficiency a soft magnetic copper microwire exhibiting the GMI effect to make the inductive coil may be used. The working principle of the MLCR sensor 215 can be explained with reference to the circuit 400 of FIG. 4.

Figure 4:
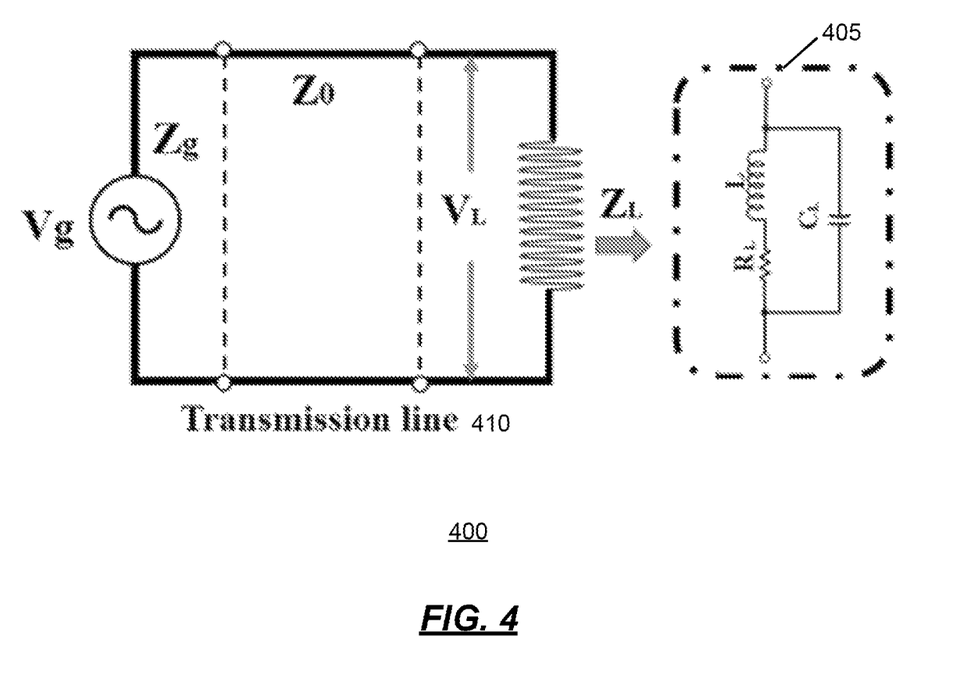
FIG. 4 is an illustration of an example circuit of a breathing monitor.

As shown in FIG. 4, the circuit 400 includes a coil 405 with a resistance ($R_L$), the series inductance (L), and the parasitic capacitance ($C_L$). The circuit 400 further includes a transmission line 410 with voltage ($V_g$), voltage ($V_L$), impedance ($Z_0$), impedance ($Z_g$), and impedance ($Z_L$). The complex impedance ($Z_{coil}$) of the coil 405 has two components, the first from the series combination of L and $R_L$ and the second from $C_L$ in parallel. Accordingly, the $Z_{coil}$ can be expressed using the following equations:

$$Z_{coil} = Z_R + Z_C \quad (1)$$

$$Z_{coil} = \cfrac{1}{\cfrac{1}{R_L + iwL} + \cfrac{1}{\frac{-i}{wC_L}}} \quad (2)$$

$$Z_{coil} = \frac{R_L + iw[L(1 + w^2 LC_L) - C_L R_L^2]}{(1 - w^2 LC_L)^2 + (wC_L R_L)^2}, \quad (3)$$

where $Z_{coil}$ is the impedance of the coil 405, w is the angular frequency, and i is the imaginary unit. Since the coiled wire of the MLCR sensor 215 is not long and has a high conductivity, the resistance of the coil 405 is so small that it may be neglected from equation (3). As a result, the impedance of the coil 405 can be approximately written as:

$$Z_{coil} \cong \frac{wL}{1 - w^2 LC_L}. \quad (4)$$

The moment at which the inductive and capacitive reactance are equal, the net current of the coil 405 becomes almost zero, which leads to the fact that the impedance becomes very large and the self-resonance occurs as an anti-resonance. The resonance frequency ($f_r$) may be calculated as follows:

$$f_r = \frac{\sqrt{1 - \left(\frac{R_L^2 C_L}{L}\right)}}{2\pi \sqrt{LC_L}}. \quad (5)$$

Accordingly, the application of an external magnetic field will cause a giant change in the impedance of the coil 405, which in turn can be exploited to make an ultrasensitive magnetic sensor such as the MLCR sensor 215.

In some embodiments, the MLCR sensor 215 may include a coil made from a soft magnetic Co-rich microwire. The coil may include approximately 10 turns of magnetic microwire wound around a quartz tube, which is 7 mm in length and has a 3 mm internal diameter. Other size tubes may be used. The microwire may be approximately ~60 μm in diameter. Other sized wires may be used. The MLCR sensor 215 may be connected to the computing device 220 that outputs the breathing data 107. The computing device 220 may include an impedance analyzer.

In some implementations, the sensor 215 may be a Hall effect sensor 215 that measures the magnitude of a magnetic field. The output voltage of the Hall effect sensor 215 is directly proportional to the magnetic field strength through it. The Hall effect sensor 215 may include a single integrated circuit that consists of one general planar Hall element and two sets of vertical Hall elements. In one embodiment, the vertical Hall element may include plates of N-type silicon inserted vertically into a P-type substrate. When current flows from the center of the plate to the ends of the plate, the external magnetic field will create a current at the middle of the plate in the opposite direction. By placing these elements in an array, the Hall effect sensor 215 can measure a magnetic field along 3 axes with high sensitivity.

Returning to FIG. 1, the diagnosis system 110 may include a diagnosis engine 120, a model 130, and a training engine 140. More or fewer components may be supported.

Figure 7:
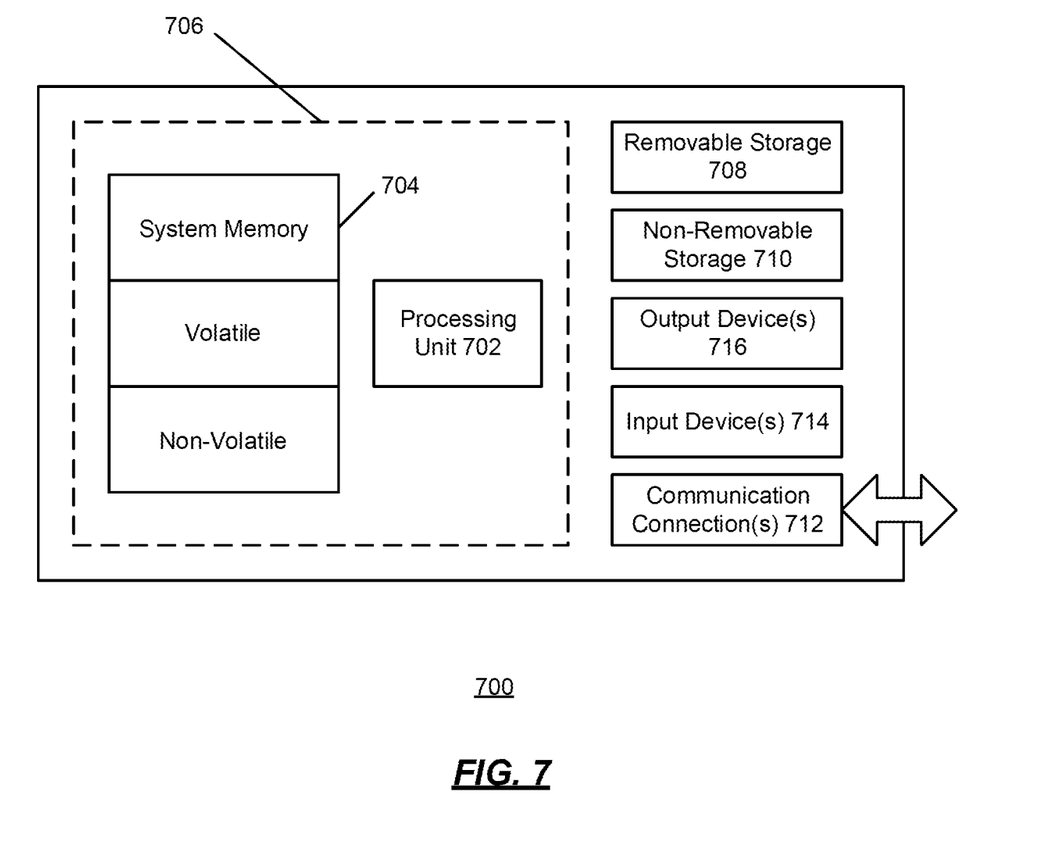
FIG. 7 shows an exemplary computing environment in which example embodiments and aspects may be implemented.

The diagnosis system 110 may be implemented using one or more general purpose computing devices such as the computing device 700.

The diagnosis engine 120 may receive breathing data 107 from the breathing monitor 105 and may use the breathing data 107 to generate a diagnosis 125. The diagnosis 125 may a diagnosis of a particular disease such as COVID-19. Other diseases may be diagnosed. Depending on the embodiment, the diagnosis 125 may include a stage along with the diagnosis. For example, with respect to COVID-19, the diagnosis 125 may indicate whether the patient associated with the breathing data 107 has stage I, stage II, or stage III COVID-19.

The diagnosis engine 120 may generate the diagnosis 125 using the breathing data 107 and one or more models 130. As discussed further with respect to the training engine 140, each model 130 may be trained to diagnose 125 a patient with a particular disease based on the breath patterns found in the breathing data 107. Each model 130 may be generated using artificial intelligence based techniques such as machine learning.

The diagnosis engine 120 may also consider what is referred to herein as medical data 109 about the patient when generating the diagnosis 125. The medical data 109 as used herein may include data that is relevant to the health of the patient such as the patient's age, weight, or BMI. The medical data 109 may further indicate any health conditions that the patient may have such as diabetes, obesity, or high blood pressure. Other health conditions may be supported.

Depending on the embodiment, the diagnosis engine 120 may generate the diagnosis 125 using the breathing data 107 and the medical data 109. In one example embodiment, some of the medical data 109 such as age may be considered by the model 130 along with the breathing data 107 when generating the diagnosis 125. In another example embodiment, there may be multiple models 130 with each model 130 trained for a different subset of patients based on medical data 109 (e.g., one model 130 for patents under 60 years old and another model for patients over 60 years old). The diagnosis engine 120 may select the model 130 to use for the diagnosis based on the medical data 109 associated with the patient.

As may be appreciated, the breathing monitor 105 can be used to remotely monitor patients for particular diseases. For example, a patient may believe that they have contracted a disease such as COVID-19. However, because of one or more issues such as the patient living in a remote location, mobility issues associated with the patient, or an advanced age of the patient, the patient may prefer to test for COVID-19 using the breathing monitor 105 and diagnosis system 110 described herein.

Accordingly, the patient may be provided the breathing monitor 105, and the breathing monitor 105 may generate and provide the breathing data 107 to the diagnosis system 110 through the network 190. The diagnosis engine 120 may then use the model 130 and breathing data 107 (and optionally the medical data 109) to generate a diagnosis 125 with respect to COVID-19. The diagnosis 125 may be provided back to patient and the patient may determine whether or not to seek additional care based on the diagnosis 125.

As another example, a patient may already have been diagnosed with an early phase of a disease such as COVID-19 (i.e., phase I) and would prefer to remain at home as long as the disease does not progress to phase II. According, the patient may be asked to periodically (e.g., while sleeping or in bed) or continuously wear the breathing monitor 105, which may transmit the breathing data 107 back to the diagnosis system 110. In the event that the diagnosis engine 120 generates a diagnosis 125 that indicates that the patient has advanced to phase II, the patient may be contacted and instructed to proceed to the hospital.

As another example, a patient may have already been admitted to a hospital for a disease such as COVID-19. The patient may be connected to the breathing monitor 105 and the breathing data 107 of the patient may be continuously used by the diagnosis engine 120 to generate a new diagnosis 125. Each diagnosis 125 may indicate whether or not the patient's condition is improving (e.g., moving from phase III to phase II) or worsening (e.g., moving from phase II to phase III). The diagnoses 125 may be used by the hospital, along with other information, to determine whether current treatments are working for the patient, or if additional treatments may be necessary.

The training engine 140 may generate and train the models 130 that are used by the diagnosis engine 120. In particular, the training engine 140 may use training data 140 collected from patients that are known to have a particular disease, as well as training data 140 collected from patients that are known not to have a particular disease.

For example, with respect to COVID-19, the breathing monitor 105 may collect breathing data 107 from patients that are known to be in one of the three phases of COVID-19 (i.e., the phases I-III). Optionally, the breathing monitor 105 may also be used to collect breathing data 107 from healthy patients that are known to not have COVID-19. The collected breathing data 107 is the training data 145 and may be used by the training engine 140 to train a model 130 to generate a diagnosis 125 based on breathing data 107.

In some embodiments, the training engine 145 may further consider medical data 109 when generating the training data 145. In particular, the training engine 145 may include some or all of the medical data 109 associated with each patient along with their breathing data 107 in training data 145 such as age, BMI, sex etc. The resulting model 130 trained using such training data 145 may then generate diagnoses 125 for patients using both the breathing data 107 and medical data 109 associated with each patient.

Alternatively, rather than use the medical data 109 as part of the training data 145, the training engine 140 may divide the training data 145 based on selected features from the medical data 109 and may train separate models 130 using the divided training data 145. The diagnosis engine 120 may then select a model 130 to use for a patient based on the medical data 109 associated with the patient.

For example, it is known that breathing patterns of individual change based on the age of the individual. School-aged children (6-18 years) breathe anywhere from 18 to 30 times per minute, an adult (18-35 years) breathes between 12 to 18 times per minute, and older people (>50 years) have respiratory rates between 16 and 25 breaths per minute. Accordingly, to better account for such differences, the training engine 140 may generate a first model 130 for diagnosing children, a second model 130 for diagnosing adults, and a third model 130 for diagnosing older people. Each model 130 may be trained using only training data 145 collected from patients in the corresponding age group. Later, when breathing data 107 is received for a patient, the diagnosis engine 120 may use the medical data 109 to determine the age of the patient and may select the model 130 corresponding to the determined age. The diagnosis engine 120 may then generate the diagnosis 125 using the breathing data 107 and the selected model 130.

The training engine 140 may further update or provide feedback to the models 130 based on the observed successes or failures of each model 130. For example, when the model 130 generates a diagnosis 125 of COVID-19 for a patient based on the breathing data 107 that does not agree with the results of a COVID-19 test, negative feedback may be provided to the model 130. Similarly, when the model 130 generates a diagnosis 125 of COVID-19 for patient based on the breathing data 107 that does agree with the results of a COVID-19 test, positive feedback may be provided to the model 130. Depending on the embodiment, the positive or negative feedback may be provided to the model 130 by adding the breathing data 107 and corresponding correct diagnosis 125 (or corrected diagnosis 125) to the training data 145 and retraining the model 130 using the updated training data 145. In this way the diagnosis system 110 may be continuously improved based on real-world data.

Figure 5:
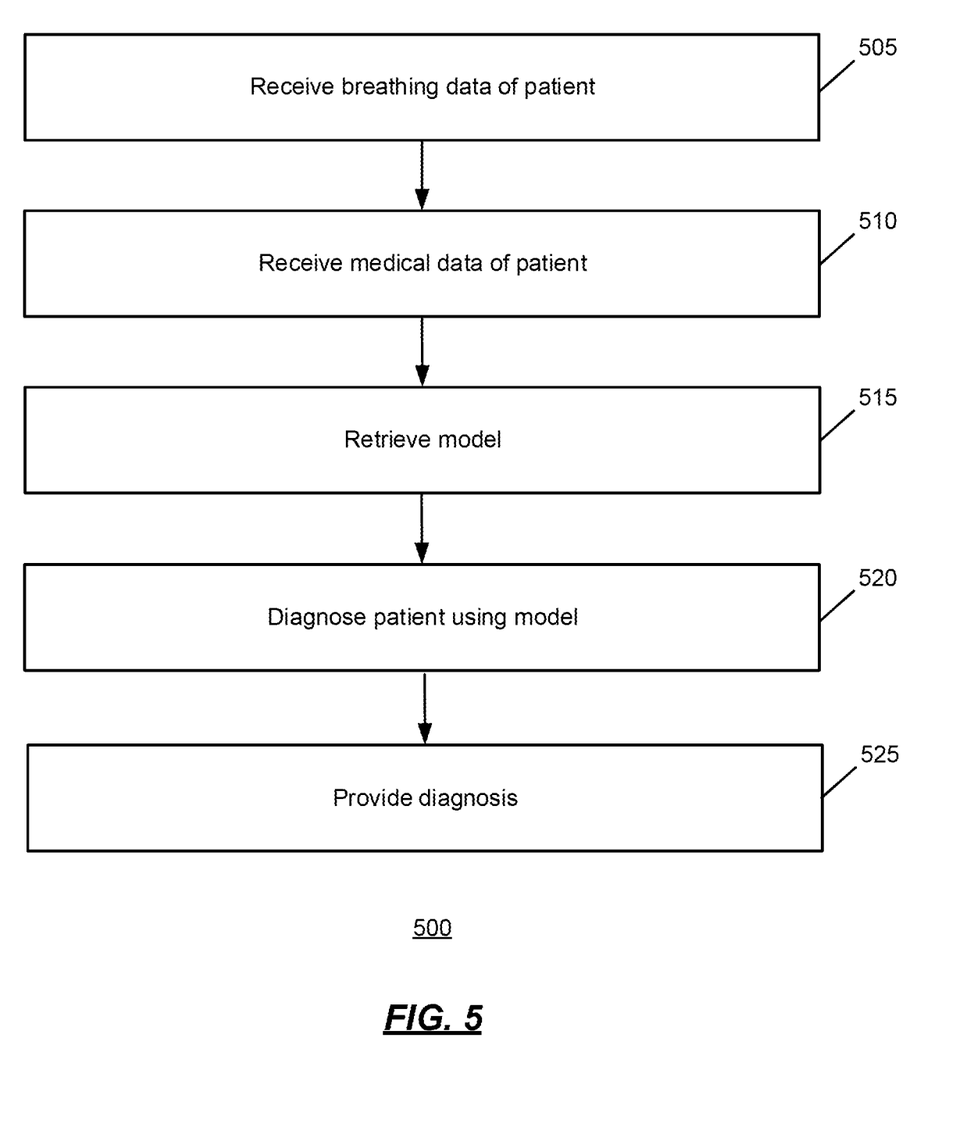
FIG. 5 is an illustration of a method for diagnosing a condition or disease based on breathing data.

FIG. 5 is an illustration of a method 500 for diagnosing a condition or disease based on breathing data. The method 500 may be implemented by the prediction system 110.

At 505, breathing data of a patient is received. The breathing data 107 may be received from a breathing monitor 105 through a network by a diagnosis system 110. The breathing monitor 105 may include a non-contact sensor 215 and a magnet 205. The magnet 205 may be affixed or placed on the chest of the patient and the sensor 215 may measure impedance as the magnet 205 moves due to the breathing of the patient. The measured impedance may be included in the breathing data 107 and may be indicative of breathing patterns associated with the patient. The sensor 215 may be a Hall effect sensor or a magneto-LC resonance sensor. Other types of sensors 215 may be used.

At 510, medical data associated with the patient is received. The medical data 109 may be received by the diagnosis system 110 through the network 190 from the breathing monitor 105. The medical data 109 may include medical characteristics of the patient including, but not limited to, age, sex, weight, height, BMI, medications taken, allergies, and current medical conditions or diseases.

At 515, a model is retrieved. The model 130 may be retrieved by the diagnosis engine 120. Depending on the embodiment, the model may be trained to diagnose a particular disease based on the breathing data 107 of a patient. The particular model 130 that is retrieved may be based in part on some of the medical data 109. For example, different models 130 may be used to diagnose the disease depending on the age of the patient or the BMI of the patient. The disease may be COVID-19 or other diseases that affect breathing.

At 520, the patient is diagnosed using the model 130. The patient may be diagnosed by the diagnosis engine 120 using the retrieved model 130, the breathing data 107, and optionally the medical data 109. The diagnosis engine 120 may generate a diagnosis 125 that indicates whether or not the patient likely has the associated disease and may also indicate a phase associated with the disease.

At 525, the diagnosis is provided. The diagnosis 125 may be provided to the patient, doctor, or other medical professional through the network. The patient (or medical professional) may then determine what actions to take based on the diagnosis 125. For example, if the diagnosis 125 is that the patient has COVID-19, the medical professional may determine that the patient should go to a hospital.

Figure 6:
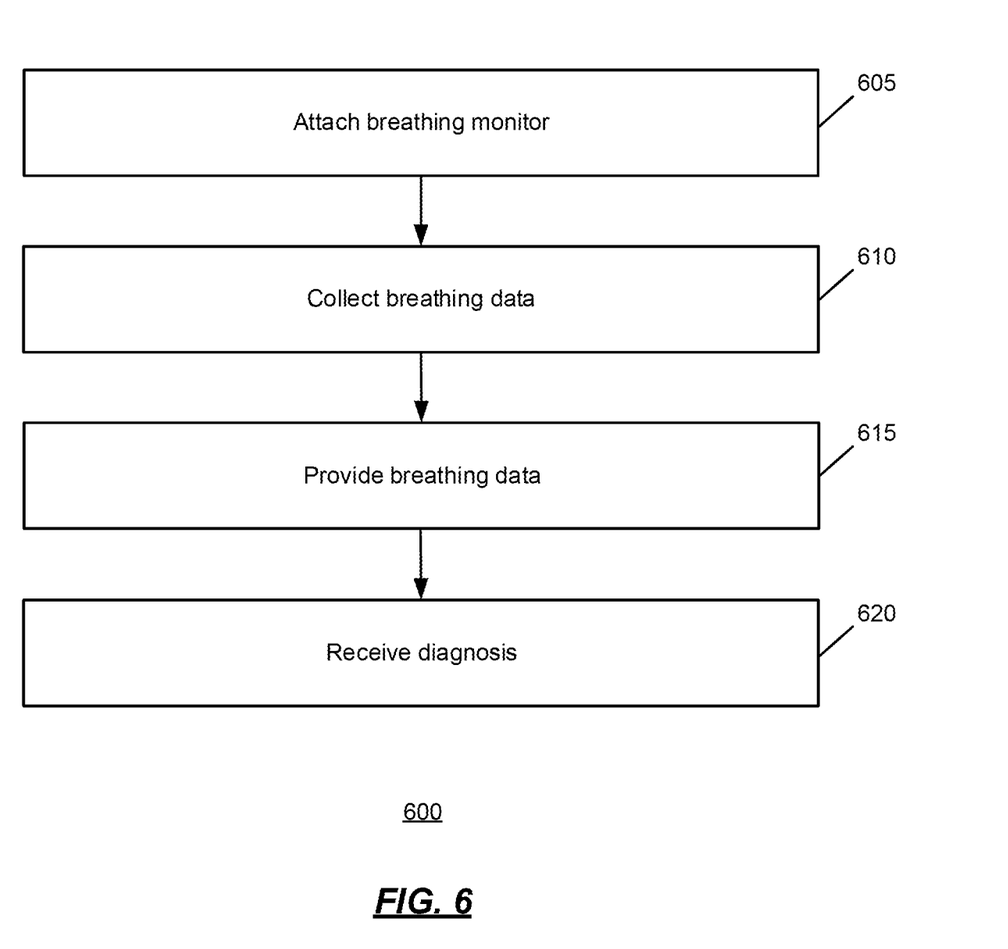
FIG. 6 is an illustration of a method for using a breathing monitor to receive a diagnosis for a disease.

FIG. 6 is an illustration of a method 600 for using a breathing monitor to receive a diagnosis for a disease. The method 600 may be implemented by the breathing monitor 105.

At 605, the breathing monitor is attached. The breathing monitor 105 may be attached to the patient by the patient themselves or by a medical provisional. The breathing monitor 105 may include a magnet 205, a sensor 215, and a computing device 220 connected to the sensor 215. The breathing monitor 105 may be attached to the patient by placing or affixing the magnet 205 to the chest of the patient. The sensor 215 may be placed approximately 5 cm from the magnet 205 but may not be in direct contact with the patient or the magnet 205.

At 610, breathing data is collected. The breathing data 107 may be collected by the breathing monitor 105. In some embodiments, as the magnet 205 moves due to the breathing of the patient, the sensor 215 may detect the movement as changes in impedance or magnetic field measured by the sensor 215. These changes are indicative of breathing patterns of the patient and may be collected as the breathing data 107. Depending on the embodiment, approximately one minute of breathing data 107 may be collected by the breathing monitor 105.

At 615, the breathing data is provided. The breathing data 107 may be provided by the breathing monitor to the diagnosis engine 120 through the network 190. The diagnosis engine 120 may receive the breathing data 107 and may use the breathing data 107 and a model 120 to generate a diagnosis 125. The diagnosis 125 may indicate whether or not the patient has a particular disease.

At 620, the diagnosis is received. The diagnosis 125 may be received by the patient and/or the breathing monitor 105. The patient may then determine what actions to take based on the received diagnosis 125.

FIG. 7 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 7, an exemplary system for implementing aspects described herein includes a computing device, such as computing device 700. In its most basic configuration, computing device 700 typically includes at least one processing unit 702 and memory 704. Depending on the exact configuration and type of computing device, memory 704 may be volatile (such as random access memory (RAM)), non-volatile (such as read-only memory (ROM), flash memory, etc.), or some combination of the two. This most basic configuration is illustrated in FIG. 7 by dashed line 706.

Computing device 700 may have additional features/functionality. For example, computing device 700 may include additional storage (removable and/or non-removable) including, but not limited to, magnetic or optical disks or tape. Such additional storage is illustrated in FIG. 7 by removable storage 708 and non-removable storage 710.

Computing device 700 typically includes a variety of computer readable media. Computer readable media can be any available media that can be accessed by the device 700 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 704, removable storage 708, and non-removable storage 710 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 700. Any such computer storage media may be part of computing device 700.

Computing device 700 may contain communication connection(s) 712 that allow the device to communicate with other devices. Computing device 700 may also have input device(s) 714 such as a keyboard, mouse, pen, voice input device, touch input device, etc. Output device(s) 716 such as a display, speakers, printer, etc. may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
a network;
a breathing monitor at a first location associated with a patient, the breathing monitor comprising:
a magnet affixed to a patient using an adhesive by the patient; and
a non-contact sensor that measures impedance caused by a magnet field associated with the magnet, wherein the breathing monitor continuously outputs breathing data indicative of a breathing pattern of the patient based on impedance measurements from the non-contact sensor and provides the breathing data to a diagnosis engine through the network; and
the diagnosis engine, at a second location not associated with the patient, that:
receives the breathing data from the non-contact sensor through the network;
receives medical data associated with the patient;
retrieves a model of a plurality of models associated with a disease based on the medical data associated with the patient, wherein each model of the plurality of models is associated with the disease and a different subset of patients based on the medical data;
diagnoses the patient with the disease using the model and the breathing data; and
in response to diagnosing the patient with the disease, provides an instruction to the patient at the first location through the network, wherein the instruction is for the patient to proceed to a hospital.

2. The system of claim 1, wherein the disease is COVID-19.

3. The system of claim 2, wherein the sensor comprises a Hall effect sensor or a magneto-LC resonance sensor.

4. A method for remote disease diagnosis based on breathing data, the method comprising:
providing a breathing monitor comprising a magnet and a non-contact sensor to a patient at a first location associated with the patient;
affixing, by the patient, the magnet to a body of the patient using an adhesive at the first location;
continuously providing breathing data of the patient by the breathing monitor to a computing device through a network, wherein the computing device is at a second location not associated with the patient;
receiving the breathing data at the computing device through the network, wherein the breathing data comprises data indicative of a breathing pattern of the patient, and wherein the breathing data comprises a waveform whose frequency and amplitude represents the breathing pattern;
retrieving a model associated with a disease by the computing device;
diagnosing the patient with the disease using the model and the breathing data; and
in response to diagnosing the patient with the disease, providing an instruction to the patient at the first location through the network, wherein the instruction is for the patient to proceed to a hospital.

5. The method of claim 4, wherein the disease is COVID-19.

6. The method of claim 4, wherein the disease is associated with a plurality of stages and each stage is associated with a different model of a plurality of models.

7. The method of claim 4, further comprising:
receiving medical data associated with the patient; and
diagnosing the patient with the disease using the model, the breathing data, and the medical data.

8. The method of claim 7, wherein the medical data comprises one or more of age and weight.

9. The method of claim 4, wherein the sensor comprises a Hall effect sensor or a magneto-LC resonance sensor.

10. The method of claim 4, further comprising:
receiving first data indicative of breathing patterns of a plurality of patients known to have the disease;
receiving second data indicative of breathing patterns of a plurality of patients known not to have the disease; and
training the model using the first and second data.

* * * * *